US00PP33803P2

(12) United States Plant Patent
Bottoms

(10) Patent No.: US PP33,803 P2
(45) Date of Patent: Jan. 4, 2022

(54) ***NYSSA* TREE NAMED 'BBN-01'**

(50) Latin Name: *Nyssa sylvatica*
Varietal Denomination: BBN-01

(71) Applicant: Dwight A. Bottoms, McMinnville, TN (US)

(72) Inventor: Dwight A. Bottoms, McMinnville, TN (US)

(73) Assignee: GREENLEAF NURSERY CO., Park Hill, OK (US)

( * ) Notice: Subject to any disclaimer, the term of this patent is extended or adjusted under 35 U.S.C. 154(b) by 0 days.

(21) Appl. No.: 17/116,262

(22) Filed: Dec. 9, 2020

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para
(74) *Attorney, Agent, or Firm* — C. Anne Whealy

(57) ABSTRACT

A new and distinct cultivar of *Nyssa* tree named 'BBN-01', characterized by its broadly ovate tree form with outwardly branching habit; vigorous growth habit; upright central leader with relatively large caliper and numerous lateral branches providing a full and densely foliated appearance; large glossy dark green-colored leaves that are initially deep red when developing and becoming dark green during the summer and turning reddish orange, red and dark red in color during the autumn; and green-colored leaf petioles variably tinged with dark red.

2 Drawing Sheets

Botanical designation: *Nyssa sylvatica.*
Cultivar denomination: 'BBN-01'.

STATEMENT REGARDING PRIOR DISCLOSURES BY INVENTOR/APPLICANT

The Inventor/Applicant hereby assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Nyssa* tree, botanically known as *Nyssa sylvatica*, commercially referred to as Upland Tupelo or Black Gum and hereinafter referred to by the name 'BBN-01'.

The new *Nyssa* tree originated from a cross-pollination made by the Inventor in Warren County, Tenn. of an unnamed selection of *Nyssa sylvatica*, not patented, as the female, or seed, parent with *Nyssa sylvatica* 'Wildfire', not patented, as the male, or pollen, parent. The new *Nyssa* tree was discovered and selected by the Inventor as a single plant within the progeny of the stated cross-pollination in a controlled nursery environment in Warren County, Tenn. during the summer of 2015.

Asexual reproduction of the new *Nyssa* tree by chip budding in a controlled environment in McMinnville, Tenn. since March, 2017, has shown that the unique features of this new *Nyssa* tree are stable and reproduced true to type in successive generations.

SUMMARY OF THE INVENTION

Trees of the new *Nyssa* have not been observed under all possible combinations of environmental and cultural conditions. The phenotype may vary somewhat with variations in environmental conditions such as temperature and light intensity without, however, any variance in genotype.

The following traits have been repeatedly observed and are determined to be the unique characteristics of 'BBN-01'. These characteristics in combination distinguish 'BBN-01' as a new and distinct *Nyssa* tree:

1. Broadly ovate tree form with outwardly branching habit.
2. Vigorous growth habit.
3. Upright central leader with relatively large caliper and numerous lateral branches providing a full and densely foliated appearance.
4. Large glossy dark green-colored leaves that are initially deep red when developing and becoming dark green during the summer and turning reddish orange, red and dark red in color during the autumn.
5. Green-colored leaf petioles variably tinged with dark red.

Trees of the new *Nyssa* can be compared to trees of the female parent selection. Trees of the new *Nyssa* differ primarily from trees of the female parent selection in the following characteristics:

1. Trees of the new *Nyssa* are more vigorous, taller and have larger caliper branches than trees of the female parent selection.
2. Trees of the new *Nyssa* have larger leaves than trees of the female parent selection.
3. Trees of the new *Nyssa* have dark green-colored leaves that are initially deep red when developing and turning orangish red, red and dark in color during the autumn whereas trees of the female parent selection have green-colored leaves turning yellowish red in color during the autumn.

Trees of the new *Nyssa* can be compared to trees of the male parent, 'Wildfire'. Trees of the new *Nyssa* differ primarily from trees of 'Wildfire' in the following characteristics:

1. Trees of the new *Nyssa* are more vigorous, taller and have larger caliper branches than trees of 'Wildfire'.
2. Trees of the new *Nyssa* have larger leaves than trees of 'Wildfire'.
3. Trees of the new *Nyssa* have dark green-colored leaves that are initially deep red when developing and turning orangish red, red and dark red in color during the autumn whereas trees of 'Wildfire' have dark green-colored leaves with red-colored apices.

Trees of the new *Nyssa* can be compared to trees of *Nyssa sylvatica* 'The James', disclosed in U.S. Plant Pat. No. 29,473. Trees of the new *Nyssa* and 'The James' differ primarily in the following characteristics:

1. Trees of the new *Nyssa* are more vigorous, taller and have larger caliper branches than trees of 'The James'.
2. Trees of the new *Nyssa* have larger leaves than trees of 'The James'.
3. Trees of the new *Nyssa* have dark green-colored leaves that are initially deep red when developing and turn orangish red, red and dark red in color during the autumn whereas trees of 'The James' have dark green-colored leaves that are light green when developing and turning orangish red in color during the autumn.

Trees of the new *Nyssa* can also be compared to trees of *Nyssa sylvatica* 'Nsuhh', disclosed in U.S. Plant Pat. No. 22,951. Trees of the new *Nyssa* and 'Nsuhh' differ primarily in the following characteristics:

1. Trees of the new *Nyssa* are more vigorous, taller and have larger caliper branches than trees of 'Nsuhh'.
2. Trees of the new *Nyssa* have larger leaves than trees of 'Nsuhh'.
3. Trees of the new *Nyssa* have dark green-colored leaves that are initially deep red when developing and turning orangish red, red and dark red in color during the autumn whereas trees of 'Nsuhh' have dark green-colored leaves that are lighter green when developing and turning orangish red in color during the autumn.

BRIEF DESCRIPTION OF THE PHOTOGRAPHS

The accompanying colored photographs illustrate the overall appearance of the new *Nyssa* tree showing the colors as true as it is reasonably possible to obtain in colored reproductions of this type. Colors in the photographs may differ slightly from the color values cited in the detailed botanical description which accurately describe the colors of the new *Nyssa* tree.

The photograph on the first sheet is a side perspective view of typical trees of 'BBN-01' grown during the early summer in an outdoor nursery.

The photograph on the second sheet is a close-up view of leaves of a typical tree of 'BBN-01' grown during the late spring.

DETAILED BOTANICAL DESCRIPTION

The aforementioned photographs and following observations, measurements and values describe trees grown in 7-gallon containers in outdoor nurseries in Park Hill, Okla. and Fort Worth, Tex. and under cultural practices typical of commercial *Nyssa* tree production. Trees used in the photographs and description were three years old. During the production of the trees, day temperatures averaged 33° C. In the following description, color references are made to The Royal Horticultural Society Colour Chart, 2015 Edition, except where general terms of ordinary dictionary significance are used.

Botanical classification: *Nyssa sylvatica* 'BBN-01'.

Parentage:

*Female, or seed, parent*.—Unnamed selection of *Nyssa sylvatica*, not patented.

*Male, or pollen, parent*.—*Nyssa sylvatica* 'Wildfire', not patented.

Propagation:

*Type*.—By chip budding the new *Nyssa* tree onto an unnamed selection of *Nyssa sylvatica* understock.

Tree description:

*Tree form and growth habit*.—Deciduous tree with broadly ovate form with outwardly branching habit; vigorous growth habit; freely branching habit with numerous lateral branches providing a full and densely foliated appearance; about 41 primary lateral branches per tree and secondary branches potentially developing at every node.

*Tree height*.—About 2.15 meters.

*Tree width (spread)*.—About 73 cm.

*Trunk caliper*.—About 3.5 cm.

*Branch angle orientation*.—Mid-tree canopy branches, about 70° to about 90° from vertical.

*Primary branch caliper*.—About 1.2 cm.

*Secondary branch caliper*.—About 7.5 mm.

*Internode length*.—About 4 cm on one-year old wood.

*Lateral branch texture*.—Smooth, glabrous.

*Mature bark texture*.—Woody; smooth, glabrous.

*Lateral branch color*.—Close to 197A to 197B.

*Mature bark color*.—Close to 197B.

Leaf description:

*Leaf buds, dormant*.—Length: About 7.5 mm. Diameter: About 4 mm. Texture and luster: Smooth, glabrous; slightly glossy. Color: Close to 187A.

*Arrangement*.—Alternate, simple.

*Length*.—About 10.4 cm.

*Width*.—About 6.25 cm.

*Shape*.—Elliptical to obovate.

*Apex*.—Acuminate with cuspidate tendencies.

*Base*.—Cuneate to obtuse.

*Margins*.—Entire.

*Venation pattern*.—Pinnate.

*Texture, upper and lower surfaces*.—Smooth, glabrous.

*Luster, upper surface*.—Glossy.

*Luster, lower surface*.—Slightly glossy.

*Color*.—When developing, upper surface: Close to 187A. When developing, lower surface: Close to 187C. Fully developed, upper surface: Darker and more green than 147A; in the autumn, variable, close to N172B to N172C, 179A or occasionally, close to 185A; venation, close to 146A. Fully developed, lower surface: Close to 146A; in the autumn, variable, close to N172D, 179B or 164A; venation, close to 145B.

*Petioles*.—Length: About 1.5 cm. Diameter: About 3 mm. Texture, upper and lower surfaces: Smooth, glabrous. Color, upper surface: Close to 144A variably overlain with close to between 46A and 53A.

Color, lower surface: Close to 145A variably overlain with close to between 46A and 53A.

Flower description: To date, flower initiation and development have not been observed on trees of the new *Nyssa*.

Temperature tolerance: Trees of the new *Nyssa* have been observed to tolerate high temperatures about 43° C. and low temperatures about −29° C. when grown in USDA Hardiness Zone 6.

Pathogen & pest resistance: To date, trees of the new *Nyssa* have not been observed to be resistant to pathogens and pests common to *Nyssa* trees.

It is claimed:

1. A new and distinct *Nyssa* tree named 'BBN-01' as illustrated and described.

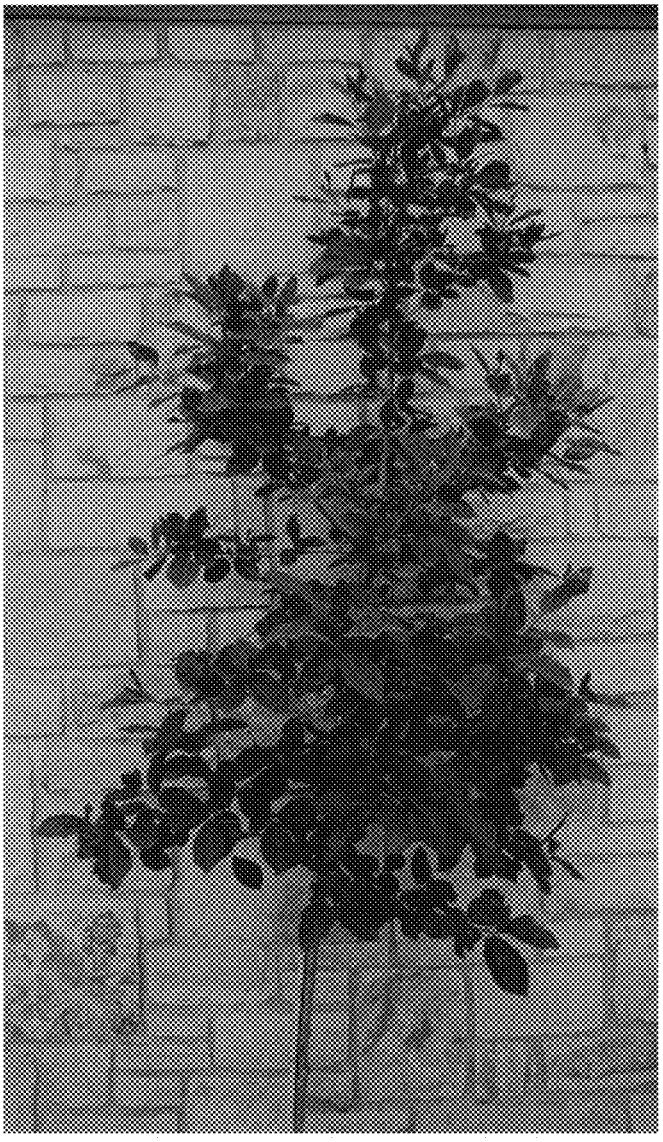

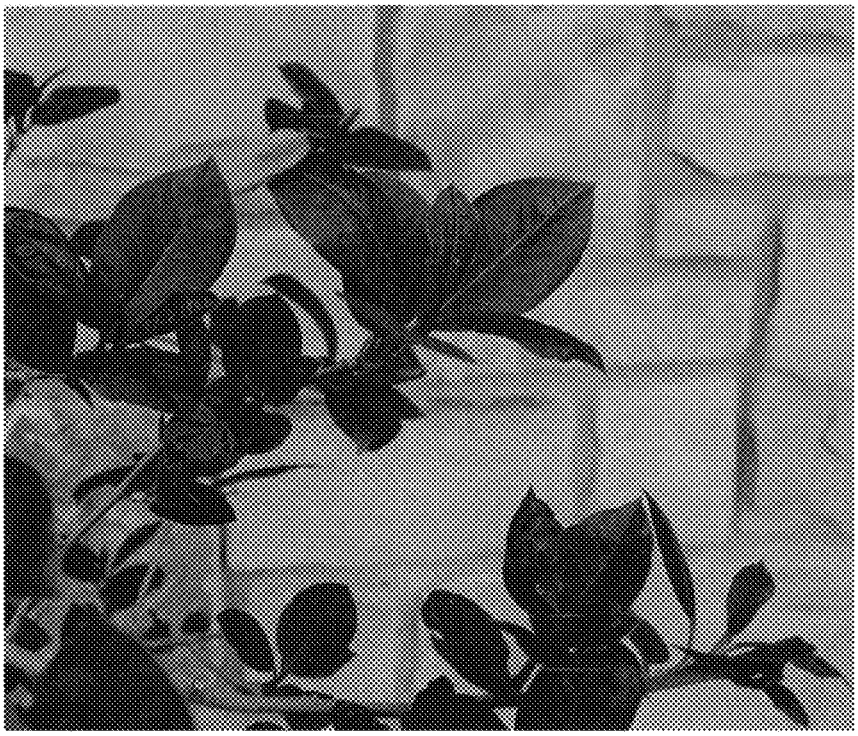

* * * * *